(12) United States Patent
McKay

(10) Patent No.: US 10,602,929 B1
(45) Date of Patent: Mar. 31, 2020

(54) SMART ATHLETIC WEAR AND RELATED METHOD OF USE

(71) Applicant: Justin McKay, Pembroke Pines, FL (US)

(72) Inventor: Justin McKay, Pembroke Pines, FL (US)

(*) Notice: Subject to any disclaimer, the term of this patent is extended or adjusted under 35 U.S.C. 154(b) by 0 days.

(21) Appl. No.: 15/952,399

(22) Filed: Apr. 13, 2018

(51) Int. Cl.
| | |
|---|---|
| *A61B 5/01* | (2006.01) |
| *A61B 5/11* | (2006.01) |
| *A41D 13/015* | (2006.01) |
| *A61B 5/00* | (2006.01) |
| *A61B 3/113* | (2006.01) |
| *A61B 5/024* | (2006.01) |
| *A61M 16/16* | (2006.01) |
| *A61M 16/10* | (2006.01) |
| *A61M 15/00* | (2006.01) |
| *A61N 1/39* | (2006.01) |
| *A42B 3/04* | (2006.01) |
| *A41D 19/00* | (2006.01) |
| *A41D 20/00* | (2006.01) |
| *A63B 71/08* | (2006.01) |

(52) U.S. Cl.
CPC ............ *A61B 5/002* (2013.01); *A41D 13/015* (2013.01); *A41D 19/0027* (2013.01); *A41D 20/00* (2013.01); *A42B 3/042* (2013.01); *A61B 3/113* (2013.01); *A61B 5/01* (2013.01); *A61B 5/024* (2013.01); *A61B 5/1116* (2013.01); *A61B 5/4875* (2013.01); *A61B 5/6803* (2013.01); *A61B 5/6804* (2013.01); *A61B 5/6806* (2013.01); *A61M 15/00* (2013.01); *A61M 16/1005* (2014.02); *A61M 16/16* (2013.01); *A61N 1/39* (2013.01); *A63B 71/085* (2013.01); *H04Q 2209/80* (2013.01)

(58) Field of Classification Search
CPC .......... A61B 5/002; A61B 5/01; A61B 5/024; A61B 5/6803–6806; A61M 16/1005; A61M 15/00; A61M 16/16; A61D 13/015; A61D 19/0027; A61D 20/00
See application file for complete search history.

(56) References Cited

U.S. PATENT DOCUMENTS

| | | | |
|---|---|---|---|
| 8,458,819 B1* | 6/2013 | Hoole | A41B 9/001 2/247 |
| 2002/0133098 A1* | 9/2002 | Shechtman | A61B 5/064 600/594 |

(Continued)

FOREIGN PATENT DOCUMENTS

WO WO2017106781 6/2017

*Primary Examiner* — Albert K Wong
(74) *Attorney, Agent, or Firm* — Allen Dyer Doppelt & Gilchrist, PA

(57) ABSTRACT

An athletic wear includes at least one of an athlete garment, a helmet, a glove, a wristband, a headband, a mouth guard, and a pad. A plurality of sensors and at least one camera are integrated into the at least one of the athlete garment, the helmet, the glove, the wristband, the headband, the mouth guard, and the pad. A processor is in signal communication with the plurality of sensors and the at least one camera for receiving, analyzing, and transmitting data signals obtained by the plurality of sensors and the at least one camera. The plurality of sensors are configured to obtain a wearer's physiological data, position data and movement data.

8 Claims, 21 Drawing Sheets

(56) References Cited

U.S. PATENT DOCUMENTS

| | | | |
|---|---|---|---|
| 2007/0209233 A1* | 9/2007 | Kim | A43B 7/082 36/27 |
| 2010/0144414 A1 | 6/2010 | Edis et al. | |
| 2011/0107618 A1* | 5/2011 | Kim | A43B 7/081 36/38 |
| 2013/0305437 A1* | 11/2013 | Weller | A42B 3/0406 2/422 |
| 2014/0070957 A1 | 3/2014 | Longinotti-Buitoni et al. | |
| 2018/0295901 A1* | 10/2018 | Kittaka | F04D 25/08 |

* cited by examiner

Figure 16
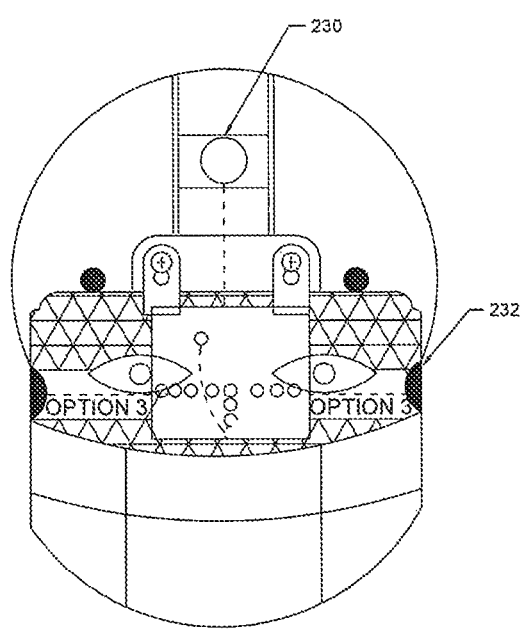
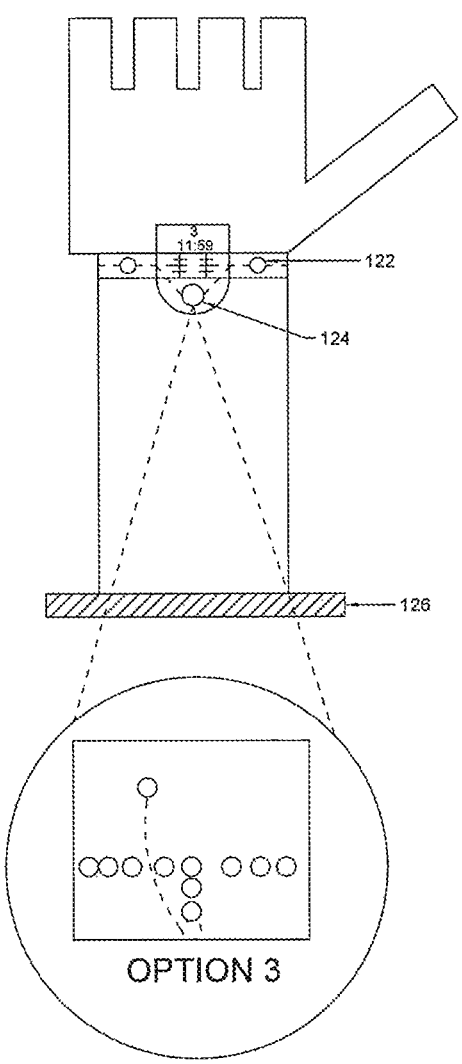

SMART ATHLETIC WEAR AND RELATED METHOD OF USE

FIELD OF THE INVENTION

This invention is directed toward athletic wear, and more particularly, to athletic wear incorporating sensors and other enhancements.

BACKGROUND OF THE INVENTION

Sports players, such as football players, soccer players and rugby players, are exposed to environmental conditions that may be harmful or life threatening. For example, extreme cold or hot weather can result in an athlete suffering from hypothermia or hyperthermia and related health conditions, for example, asthma attacks and dehydration. An athlete can also suffer from injury to a knee, ankle, muscle, bone or tendon due to excessive high jumping. An athlete can also suffer from injury to the nose, for example, damaged cartilage. Some athletes are born with small nasal passages, complicating respiration under extreme physical activity. Some improvements have been made to athletic wear to address the abovementioned concerns, but further improvements are possible.

SUMMARY OF THE INVENTION

Based on the foregoing, it is an object of the present invention to provide a violation-detection apparatus and a related method of use. According to an embodiment of the present invention, the invention is directed to athletic wear that includes at least one of an athletic garment, a helmet, a glove, a wristband, a headband, a mouth guard, and a pad. A plurality of sensors and at least one camera are integrated into the at least one athletic garment, helmet, glove, wristband, headband, mouth guard or pad. A processor is in signal communication with the plurality of sensors and the at least one camera for analyzing data signals obtained by the plurality of sensors and the at least one camera and determining athlete performance statistics, athlete physical conditions and sport data in real time. The plurality of sensors are configured to obtain data on the wearer's position, motion and physiological status.

According to another embodiment of the present invention, athletic wear includes at least one of an athlete garment, a helmet, a glove, a wristband, a headband, a mouth guard, and a pad. A plurality of sensors are integrated into the at least one athletic garment, helmet, glove, wristband, headband, mouth guard and pad. One or more cameras configured to capture one or more images of a sports scene are integrated into at least one of the athletic garment and the helmet. At least one dispenser system is configured to provide medication and water to a wearer. One or more wind force aerodynamic slots are configured to be controlled by the wearer as needed. One or more ball joints and axles are configured to protect and massage a wearer's muscle, tendon, and bone. A processor is in signal communication with the plurality of sensors configured for analyzing signals generated by the plurality of sensors, the at least one camera, the at least one dispenser system, the dispenser system, the one or more wind force aerodynamic slots, and the one or more ball joints and rubble axles. The processor is configured for analyzing signals generated by the plurality of sensors and determining athlete performance statistics, athlete physical conditions and sport data in real time. The plurality of sensors include one or more impact sensors, trajectory sensors, low-air inflatable sensors, eye-tracking sensors, pressure sensors, dehydration sensors, electromagnetic-field sensors, ultrasonic sensors, anemometers, and thermometers, sensors to detect a level of a specific substance, heart-rate sensors, and dehydration sensors configured to obtain data on at least one of a wearer's position, motion and physiological status.

BRIEF DESCRIPTION OF THE DRAWINGS

For a fuller understanding of the invention, reference is made to the following detailed description, taken in connection with the accompanying drawings illustrating various embodiments of the present invention, in which:

FIG. 16 is a diagram of an athlete's wristband having kinesthetic astral projection, according to another embodiment of the present invention;

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
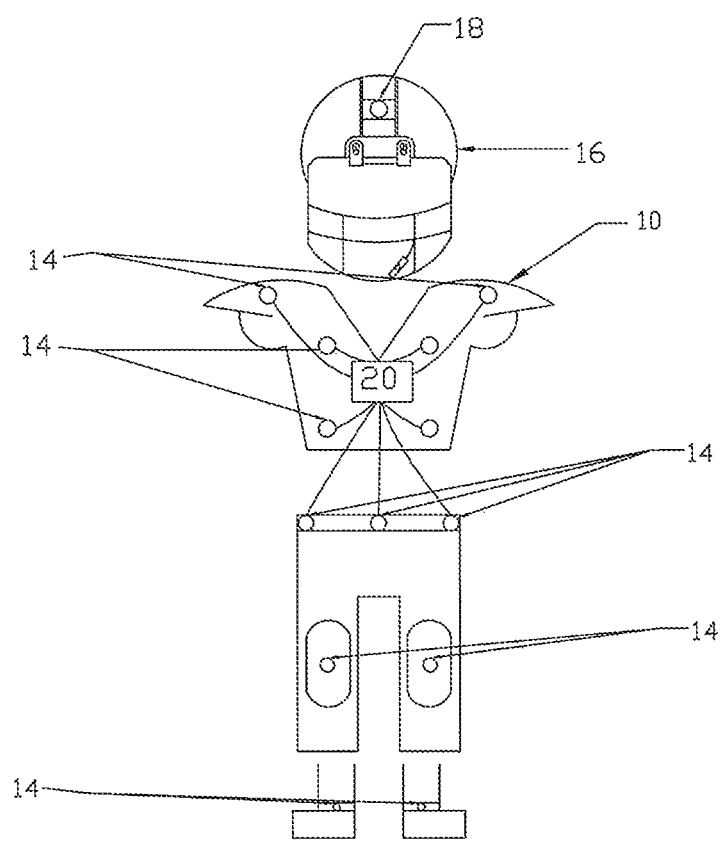
FIG. 1 is a front view of an athlete's garment integrating a plurality of sensors and a camera, according to one embodiment of the present invention.

FIG. 1 illustrates athletic wear 10 including a garment 12 and a plurality of sensors 14. In the depicted embodiment, the plurality of sensors 14 are placed on one or more pads (e.g., shoulder pads, chest pads, thigh pads, elbow pads, and knee pads) of the garment 12. For example, the plurality of sensors can include an impact sensor, a trajectory sensor, a possession sensor, an eye tracking sensor, a pressure sensor, a dehydration sensor, an electromagnetic field sensor, an anemometer, and a thermometer, an inertial sensor, a GPS position sensor, a low water sensor, a low aerosol inhaler sensor, a hyperthermia sensor, a hypothermia sensor, and an air pad inflatable sensor and the like.

Each sensor is configured to obtain a wearer's physiological data (e.g., saliva levels, blood pressure levels, heart rate, pulse), position data, movement data (e.g. running, resting) and other sport related data. The data can be used by coaches, referees, other team members, and fans. For example, a low-water sensor is configured to detect if an athlete's water bottle is low on water and needs to be refilled. As another example, dehydration sensors are configured to detect if a player may possibly be dehydrated. As another example, a low aerosol inhaler sensor is configured to detect if an aerosol inhaler is low on medication for preventing an asthma attack. As another example, a hyperthermia sensor is configured to detect if an athlete's body temperature is higher than normal. If the temperature is higher than normal, the garment can be configured to provide cooling to one or more air pads and thus to combat against hyperthermia. If an athlete has a body temperature below normal, the garment can release heat to one or more air pads located on the athlete's body and thus to combat against hypothermia. As another example, one or more air pad inflation sensors are configured to detect the pressure inside one or more air pads in the garment. The air pad pressure should be above a threshold to absorb impact, lowering the risk of injury. An anemometer is configured to obtain data on how an impact, a tackle, and/or a hit affects a wearer. A pressure sensor is configured to detect involuntary movements in the body such as twitching and fluttering, which may provide evidence of a possible stroke or dehydration. The details of the sensors will be described in detail in the following figures.

The athletic wear 10 can also include a helmet 16 incorporating at least one camera 18. The camera 18 can work cooperatively with an electromagnetic field sensor on the athletic wear 10 to capture images while the electromagnetic field sensor detects the breaking of a location barrier. Other types of violation can be detected, for example, blocking below the waist, blocking in the back, clipping, chop blocking, delaying the game, encroachment, an equipment violation, face masking, false start, helmet-to-helmet collision, holding, horse collar tackle, illegal batting, illegal contact, illegal formation, illegal forward pass, illegal hands to face, illegal kick, illegal kickoff, illegal motion, illegal participation, illegal shift, substitution infraction, illegal substitution, illegal touching of a forward pass, illegal touching of a free kick, illegal touching of a scrimmage kick, illegal use of hands, ineligible receiver downfield, intentional grounding, leaping, leverage, neutral zone infraction, offside palpably unfair act, pass interference, personal foul, roughing the passer, roughing a kicker, roughing a snapper, running into a kicker, sideline infraction, spearing, targeting, tripping, and the like.

The plurality of sensors (e.g., sensors 14) and at least one camera (e.g., camera 18) are in signal communication with a processor 20 configured for transmitting, receiving, and analyzing data signals generated by the plurality of sensors. The data obtained by the plurality of sensors and/or processed by the processor are used for assessing athlete health condition, gathering performance data and detecting or determining a rule infraction. In the depicted embodiment, the processor 20 is a microprocessor positioned on the athletic garment 12. However, the processor 20 can be located remotely from the athletic garment 12 (e.g., in close proximity to a sport field), and the plurality of sensors 14 and the at least one camera 18 can communicate wirelessly with the processor 20.

Figure 2:
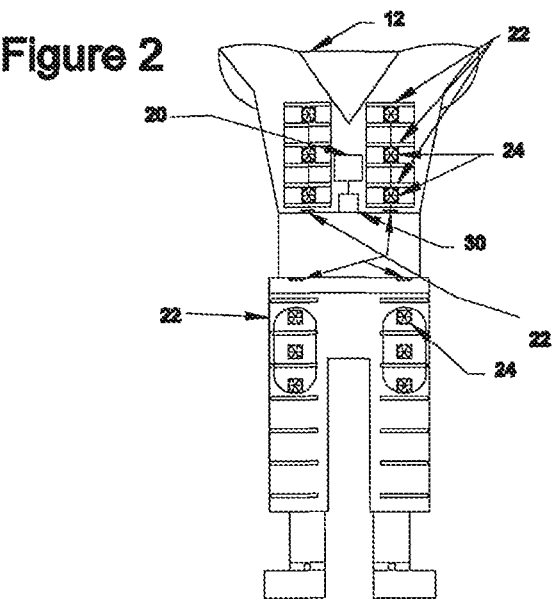
FIG. 2 is a front view of an athlete's garment integrating a plurality of aerodynamic slots, according to another embodiment of the present invention.

Referring to FIG. 2, an example athletic garment 12 is illustrated. The athletic garment 12 includes a plurality of aerodynamic slots 22 configured to pass through air to decrease the drag force while the player is moving rapidly. The aerodynamic slots 22 can be closed and opened by a wearer as desired. The status of the one or more dynamic slots 22 are also connected to a processor (e.g., processor 20) mounted on the garment 12 via a wired or wireless connection. The processor 20 can correlate athlete position data and athlete performance data to determine the best time to open or close a specific aerodynamics slot while the athlete is in motion. A plurality of micro fans 24 are installed on the athletic garment 12 to cool down a wearer and decrease the likelihood of hyperthermia. The plurality of micro fans 22 are preferably mounted on air pad foam that can absorb impacts.

Figure 3:
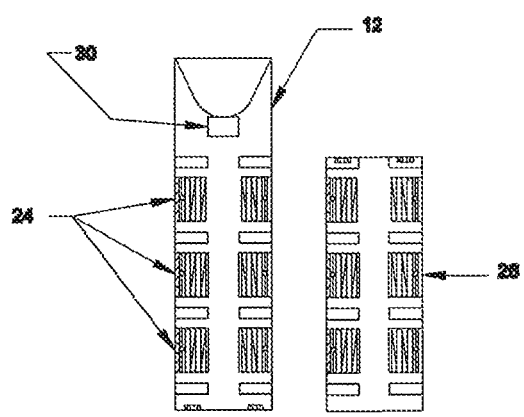
FIG. 3 is a side view of an athlete's garment integrating a plurality of micro springs, according to another embodiment of the present invention.

FIG. 3 is a side view of another example athletic garment 12. The garment 12 includes a plurality of helix wave micro springs 26 configured to absorb impacts when a wearer makes contact with another athlete or the ground. A plurality of micro fans 24 can also be mounted in close proximity to the helix wave micro springs 26. FIGS. 2 and 3 also show a radio frequency transceiver 30 for transmitting to and/or receiving data between the plurality of sensors 14, the at least one camera 18, the aerodynamic slots 22, and the processor 20.

Figure 4:
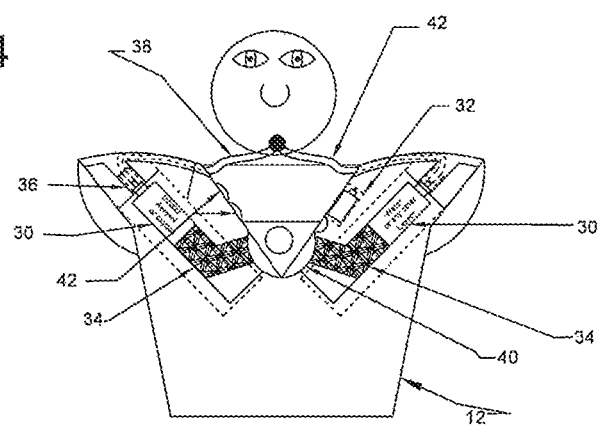
FIG. 4 is a front view of an athlete's garment integrating a plurality pockets for storing water and medication, according to another embodiment of the present invention.

FIG. 4 illustrates an athletic garment 12 integrated with at least one pocket 30 for storing and dispensing water and/or other medications for asthma, shortness of breath, chronic obstructive pulmonary disease (COPD), chronic bronchitis, or other conditions. The at least one pocket 30 (e.g., water or liquid picket) can be opened and closed via a door made of Velcro material or other materials. For example, a medication can be dispensed by pushing a medication dispensing button 32, which can in turn extend and expand a spring 34 to dispense a medication. A medication can be dispensed to a socket 36 and travel through a minute tube 38 to a wearer's mouth. The tube 38 can be extended as desired. The athlete can thus inhale medication as needed. The medical dispensing button 32 can also be used for dispensing other substances such as epipen or insulin if the player is in contact with food, liquids, fragrances, and the like. If an athlete is experiencing shortness of breath, the inhaler aerosol can be replaced with an oxygen aerosol. A similar design can be used for the water dispenser system.

Figure 5:
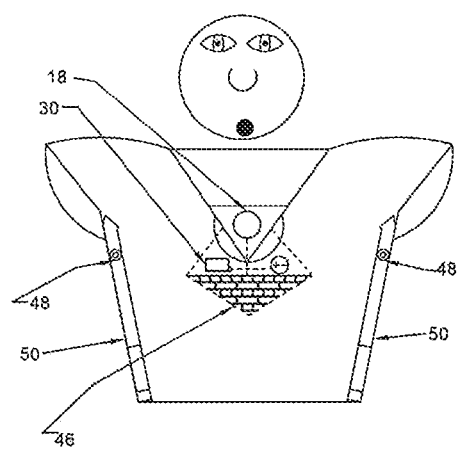
FIG. 5 is a front view of an athlete's garment integrating a defibrillator and a water and air dispensing system, according to another embodiment of the present invention.

FIG. 5 shows an athletic garment 12 (e.g., upper body suit) having one or more of a camera 18, a RF transceiver 30, a defibrillator 46, and a speaker 42 on the front side of the garment 12. The defibrillator 46 is configured to detect if an athlete has an irregular heartbeat or heart palpitations. The heart condition can be verbally communicated to an athlete through a speaker located on the jumpsuit jacket or helmet. If the event of a stroke or heart attack, the defibrillator 46 can deliver a mild to medium electrical shock to the heart of the athlete through the electrodes and thus help to stabilize the heart until professional medical treatment is available. The garment 12 can include sunblock mist release button 48 to release an air, water, and sunblock from mist reservoir 50, thereby cooling down the athlete's arms and decreasing hyperpigmentation and risk of skin cancer. The speaker 42 is configured for a wearer to communicate to teammates and/or coaching staff during and after a gameplay.

The cameras 18 on the chest of the athletic garment 12 are configured to capture images from the perspective of a wearer. The camera 18 can allow an audience to follow an athlete during a game. The camera 18 can be used for the benefit of fans who do not enjoy a superior vantage point, enabling them to follow an athlete and the game being played. The video data captured by the cameras can also be used by the referee in the review of alleged penalties. The camera 18 can also be configured to detect contact points in a collision. For example, in the case of a head on collision, a contact point on the helmet can be become illuminated. The camera 18 can also be configured to take a picture and record video of the head after a collision for coaching staff and referees to view. Data obtained by the defibrillator 46 and camera 18 can be transmitted to fans, referee, and coaches about a specific athlete's physical condition and inform the decisions of medical personnel.

Figure 6:
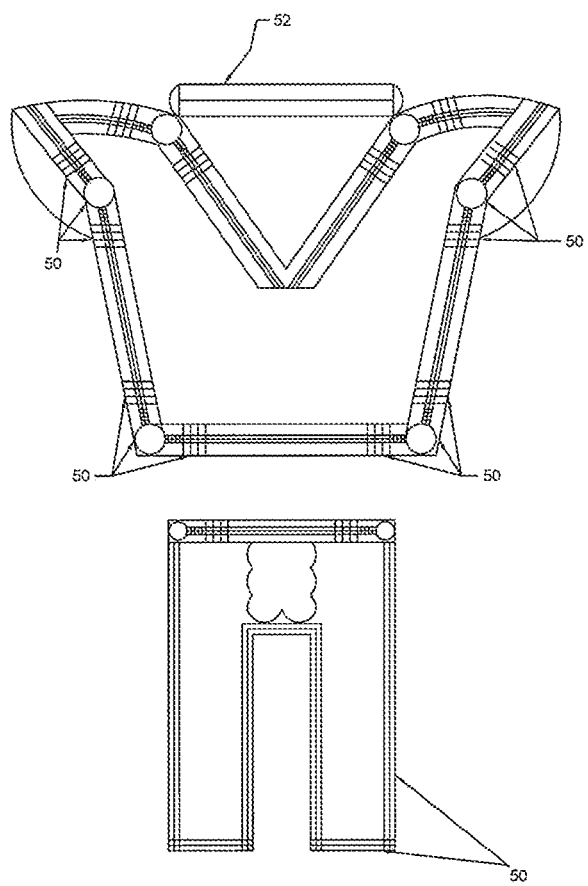
FIG. 6 is a front view of an athlete's garment integrating one or more rubber and foam ball joints and axles, according to another embodiment of the present invention.

Referring to FIG. 6, the athletic garment 12 includes one or more rubber and foam ball joints and rubber axles 50 configured to react as tendons and bones that flex in motion to protect a wearer's muscles, tendons, and bones. The athletic garment 12 can also include a neck massager 52 configured to wrap around a wearer's neck upon the players motion. As an example, the neck massager 52 can be made out of flexible material such as foam, rubber, air pad, and the like, that can bend and flex in motion. If a wearer bends his neck down, the neck massager 56 can contract and wrap the wearer's neck. When the wearer puts his neck back up in an erect position, the neck massager 52 can expand and release athlete's neck muscles and jugular vein, protecting the athlete's neck and collar bone area from injury. If the wearer goes airborne and can't control his landing, the neck massager 52 can be used to protect his neck muscles, collar bone, tendons, and jugular vein from injury.

Figure 7:
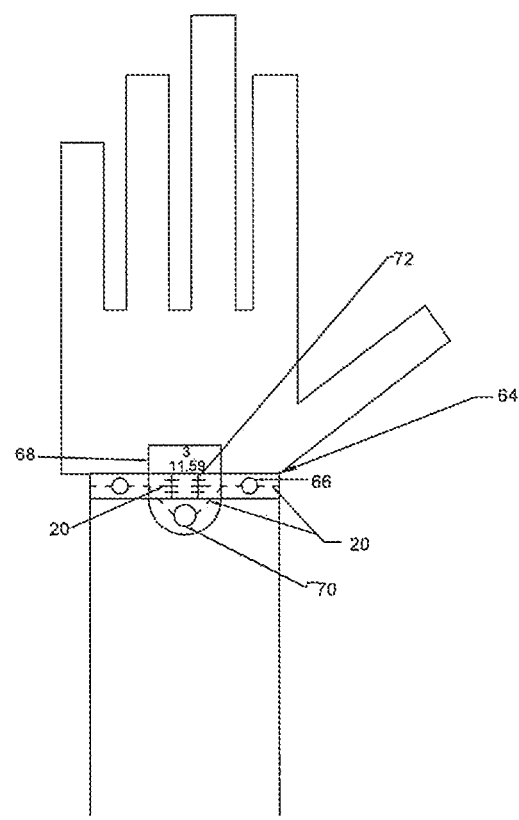
FIG. 7 is a front view of an athlete's wristband integrating at least one sensor, according to another embodiment of the present invention.

Referring to FIG. 7, the athletic wear 10 also includes a wristband 64. The wristband 64 includes a pulse sensor 66 and a radio frequency transceiver 20 connected thereto. Data received by the pulse sensor 66 can be transmitted to one or more referees, sideline monitors, and the like, via the transceiver 20. The wristband 64 also has a timeout button 70 connected to the transceiver 20 to call a time out. A time-out call will be transmitted to one or more referees and coaches via Bluetooth or another suitable wireless communication method. This will decrease the delay and/or mistake of a time-out request from a player. The timeout button 70 can include a shot clock timer and gameplay remaining timer screen that can inform a wearer of game time information such as time left for gameplay and remaining timeouts. The wristband 64 also includes a defibrillator shock sensor 72 that can detect the pulse of a wearer. When an athlete wearer experiences a heart attack, heart palpitations, or general weakness and isn't responding, the pulse sensor 72 can detect if the player has a pulse. The wristband 64 can have a display screen 68 configured to show the number of timeouts available and number of fouls the athlete has acquired.

Figure 8:
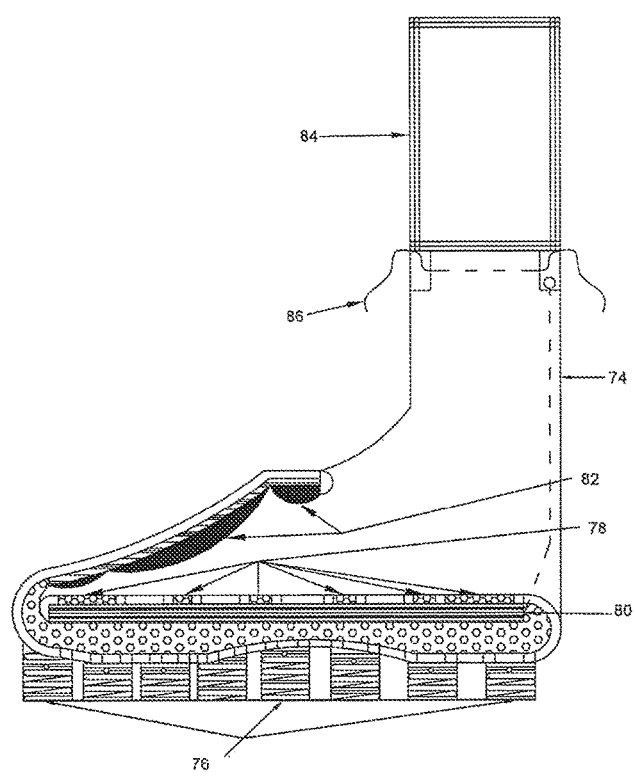
FIG. 8 is a side view of an athlete's foot sleeve integrating one or more sensors and micro springs, according to another embodiment of the present invention.
Figure 9:
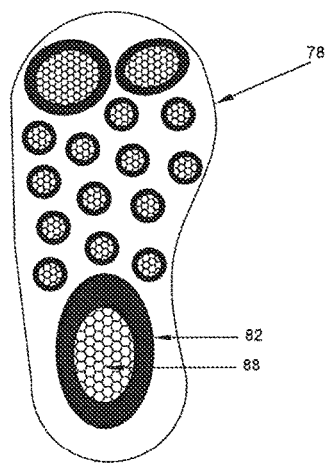
FIG. 9 is a bottom view of the athlete's foot sleeve of FIG. 10.

FIGS. 8-9 illustrate a foot sleeve 74 inside a wearer's shoe. The foot sleeve 74 is configured to absorb impact when a wearer jumps and lands on her feet, decreasing injury to the player's ankle, knees, muscles, tendons, and the like. The foot sleeve 74 can extend all the up to the player's knee. The foot sleeve 74 includes one or more helix microwave springs 76 function as shocks absorbers. The foot sleeve 74 also has a foam and gel insole 78 to absorb the impact from the helix microwave springs 76 so an athlete won't feel the impact from the helix microwave springs 76. The foot sleeve 74 also has massage sensors 80 that can massage an athlete's foot and ankles such that an athlete's foot, muscles, tendons, and ankle will stay relaxed.

The foot sleeve 74 also has a gel therapeutic insole 78 that protects the top and bottom of the foot during running and impact, decreasing injuries to the foot muscles, tendons and ankle. The foot sleeve 74 has a massage switch that connects to the massage sensors 80 by power wires connected to a battery. The player can summon the massage sensors 80 to turn on and off by pressing the power button.

The foot sleeve 74 can extend up to a wearer's knee and anterior cruciate ligament (ACL). The foot sleeve 74 includes massager 84 that will flex and keep the knee and ACL intact upon motion and will transfer all weight and tension from the player's ankle, knee, and ACL to decrease injuries. The foot sleeve 74 also has an ankle shoestring shoelace 86 than can strap the foot sleeve and tie it down so the foot sleeve will not slip or move during motion.

FIG. 9 illustrates a gel therapeutic insole 78 of the inside of the foot sleeve 74. The insole includes a plurality of rubber patches 88 surrounded by memory foam 82. The design is effective for transferring all weight on the toes and foot of the athlete and absorbing impacts to decrease injuries of the foot, ankles, knee and ACL. This design will strengthen the memory foam and rubber and allow the memory foam to conform to the design of a player's foot and combat pain related to flat footedness.

Figure 10:
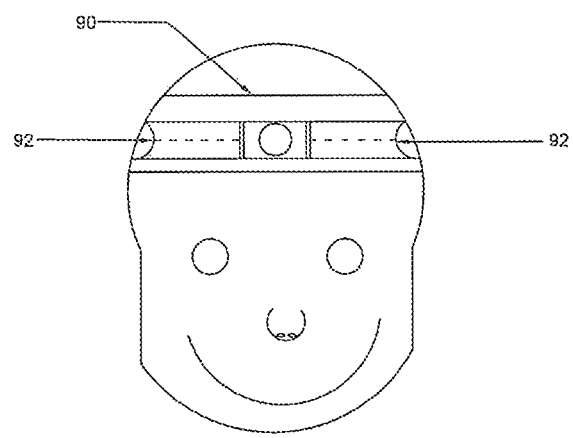
FIG. 10 is a front view of an athlete's headband integrating a pulse sensor and a massager, according to another embodiment of the present invention.

FIG. 10 illustrates a headband 90 including at least one massager incorporated with a pulse sensor 92. The massager can massage a wearer's head and temple areas to relax the wearer's nerves. The pulse sensor 92 is configured to detect the wearer's pulse in the temple area. The pulse sensor 92 is useful in case the wearer should suffer a stroke, heart attack, heart palpitations, the wearer is unresponsive and no pulse can be obtained from a wrist. The pulse sensor 92 on the headband 90 along with sensors 14 on the garment 12 can determine a wearer's overall physical condition.

Figure 11:
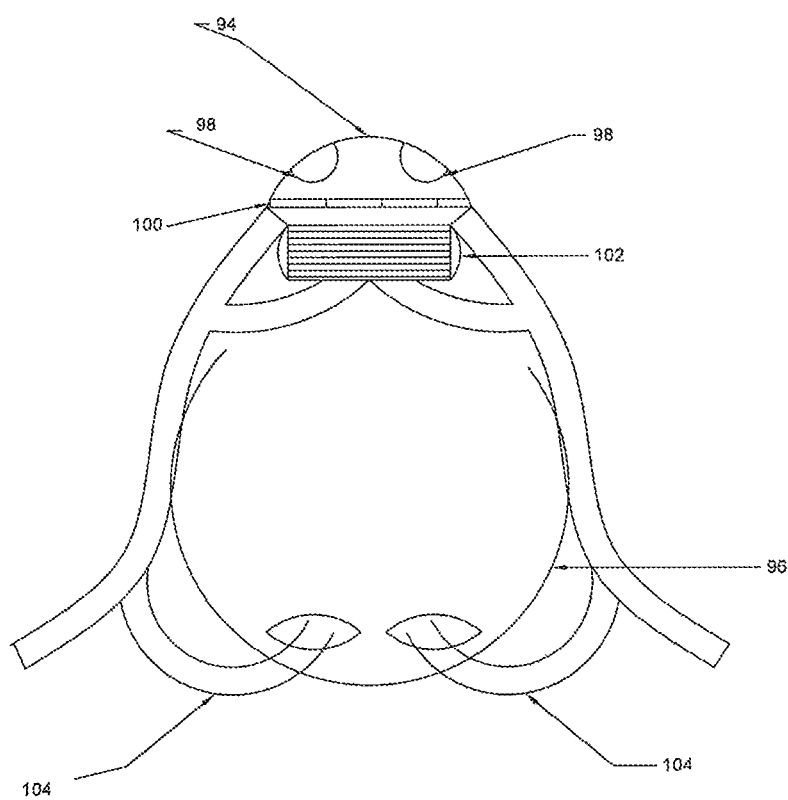
FIG. 11 is a top view of an athlete's nostril air humidifier and oxygen supplier, according to another embodiment of the present invention.

FIG. 11 illustrates a nostril air humidifier and oxygen supplier 94 configured to be attached to protect the wearer's nose 96 from damage and provide fresh clean air to the wearer's nose 96 and to the lungs. The nostril air humidifier 94 can purify the air of dust, pollen, fragrances and etc. The nostril air humidifier and oxygen supplier 94 includes an air intake opening 98 configured to intake oxygen when the player inhales through the nose. The nostril air humidifier and oxygen supplier 94 also includes a ram air oxygen fan 100 configured to spin clockwise by a wearer's inhaling motion, thereby pushing air through an intake cone air filter 102 to purify the air. Clean air can be delivered through an air intake hose 104. When an athlete exhales carbon dioxide, the ram air fan 100 will spin counter-clockwise and push the air out through the air intake opening 98. This nostril air humidifier and oxygen supplier 94 can ensure that a wearer will have sufficient clean oxygen at all times.

Figure 12:
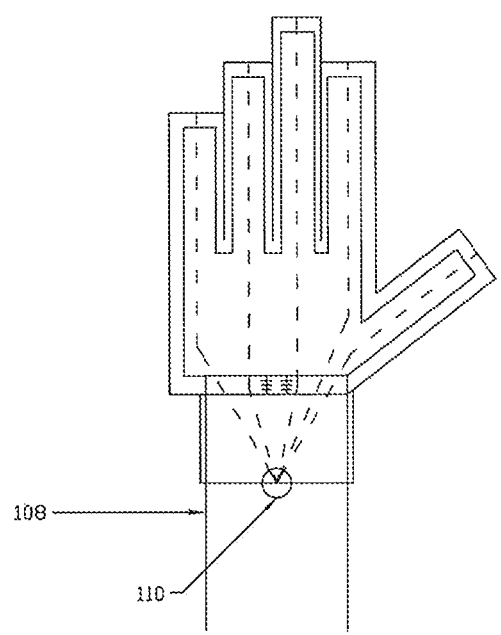
FIG. 12 is a diagram of an athlete's glove, according to another embodiment of the present invention.

FIG. 12 illustrates an athlete's glove 108 configured to assist a player in grabbing and tackling other players. The glove 108 includes a hand tension dialer 110 configured to adjust (e.g., expand or contract) string tension in the pinky finger, ring finger, middle finger, index finger, and thumb. The hand tension dialer 110 can open a wearer's hand without the wearer applying pressure. The hand tension dialer 110 can be used to achieve a comfortable position for the hand so the player won't have to open and close the hand to catch a ball, resulting in faster, more accurate results.

Figure 13:
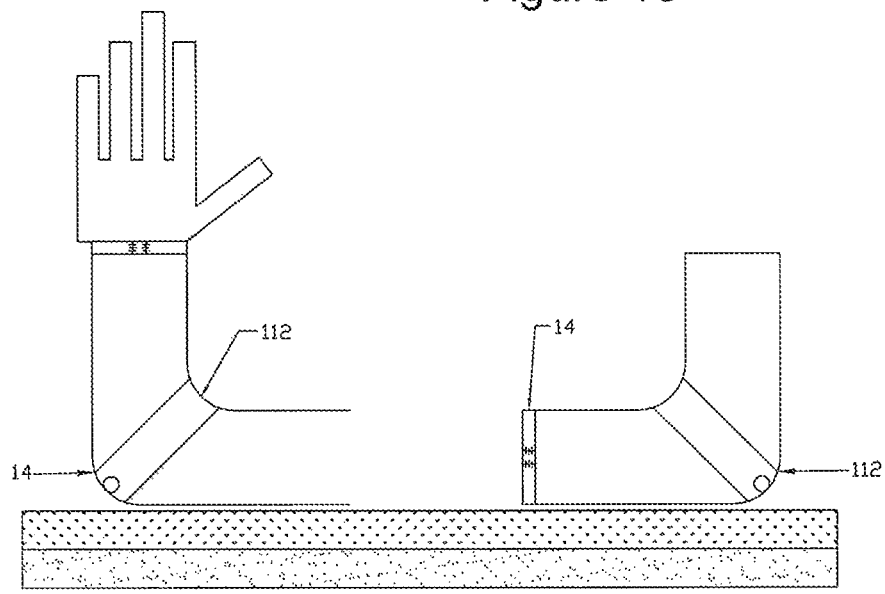
FIG. 13 is a diagram of a wristband and elbow band incorporating one or more sensors, according to another embodiment of the present invention.

FIG. 13 illustrates a plurality of position sensors 14 on an elbow band and a knee band. The plurality of position sensors 14 can detect when an offensive player has possession of a football. The plurality of sensors 14 will help a referee to determine if an offensive player caught a ball (e.g., football) before or after another event that influence the course of a game. A plurality of position sensors 14 on a knee band 112 of a player can determine when and where the player kneeled if a ball is in an offensive player's possession. For example, an elbow band 112 with a plurality of position sensors 14 can also detect if a wearer's elbow has fallen on the ground when a wearer has possession of the football. The plurality of position sensors 14 can also be used to determine if a catch is in close proximity to a boundary line. For example, the plurality of sensors 14 can determine if the offensive or defensive player has caught a ball with both feet inbounds before running or landing out of bounds.

Figure 14:
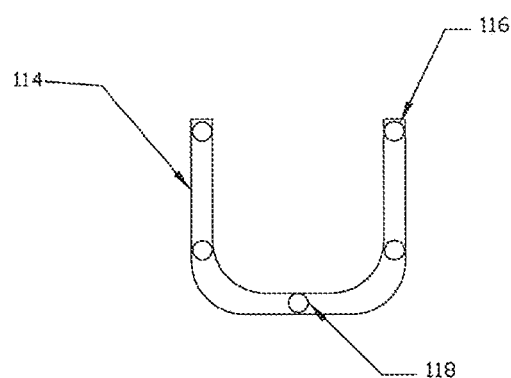
FIG. 14 is a diagram of an athlete's mouth piece incorporating one or more sensors, according to another embodiment of the present invention.

FIG. 14 illustrates a mouthguard 114 that includes a dehydration sensor 116 configured to determine dryness of a wearer's mouth. For example, if a certain amount of saliva is not produced in the wearer's mouth, then the wearer's mouth is excessively dry. The mouthguard 114 also includes a thermometer 118 configured to check the wearer's temperature. The physical condition data collected by the mouth guard 114 can be transmitted to a member coaching staff, a water boy, and others if the condition is abnormal. The player will also be notified of the need for water through the speaker in the helmet.

Figure 15:
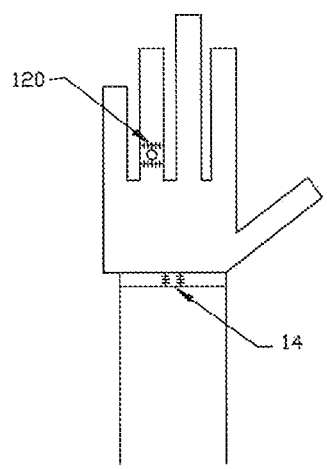
FIG. 15 is a diagram of an athlete's snap ring sensor, according to another embodiment of the present invention.

FIG. 15 illustrates snap ring sensor 120 on a wearer's finger. The snap ring sensor 120 is configured to detect a snap. Specifically, a plurality of sensors (e.g., motion sensors, vibration sensors, and trajectory sensors) in a ball (e.g., football) can communicate with the snap ring sensor 120 and a location sensor 14 on a wristband to detect the point of tackle and determine when and how a ball center was hit by a defensive player.

FIG. 16 illustrates a wristband 122 having a kinesthetic astral projection function. The wristband 122 can be used on sidelines during huddles so all players can review impromptu plays. The wristband 122 includes a micro projecting camera 124 configured to show a sports game on the floor as a 2D view and/or show an astral projection in a 3D view by emitting a projection from the wristband onto a plexiglass 126 having flex points to transform a 2D image into a 3D astral projection.

Figure 17:
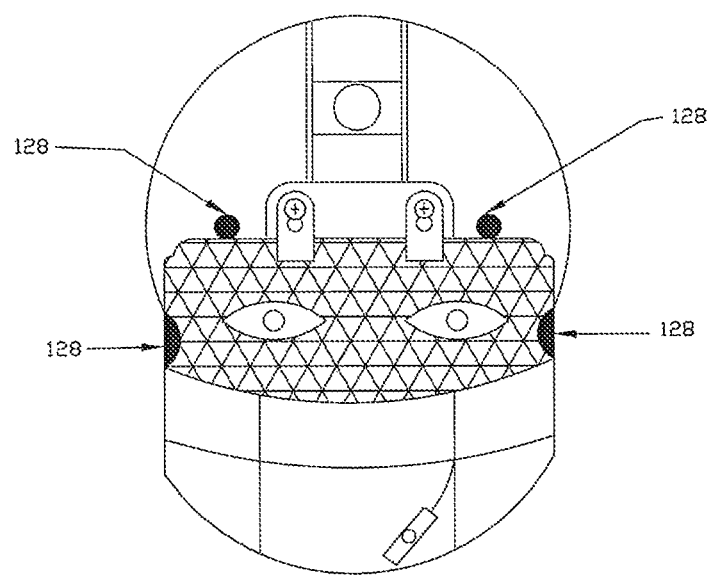
FIG. 17 is a diagram of an athlete helmet incorporating one or more sensors, according to another embodiment of the present invention.

FIG. 17 illustrates a helmet incorporated with one or more eye movement sensors 128 configured to monitor eye movement. When a player is in pain, he may close his eyes aggressively for a while or simultaneously. A wearer may also bite the mouth guard aggressively and a pressure sensor in the mouth guard will detect the biting action. A processor (not shown) connected to the plurality of eye movement sensors 128 and pressure sensor can determine whether a player is in pain and send a signal to inform a member of the coaching staff. When a concussion has occurred, the eye movement sensors 128 can also determine if the eyes have stayed open for an extended period of time, suggesting possible brain injury and vision or eye disturbances. The eye movement sensor 128 will also be able to detect if a player has suffered from a concussion, heart attack, or stroke through the symptoms of detecting if the eye is remaining open for long periods of time without any movement. Rapid eye movement or fluttering will suggest a player may possibly be suffering from a seizure. Additionally, the eye movement sensors 128 can detect if a player has facial drooping, suggesting that the player could have the signs of suffering from a stroke. The eye movement sensors 128 will also be able to detect if a player has intentionally violated any penalties. For example, if the eye movement sensors 128 detect a defensive player has clipped an offensive player and has made eye contact before the clipping event, the event can be interpreted as intentional.

Figure 18:
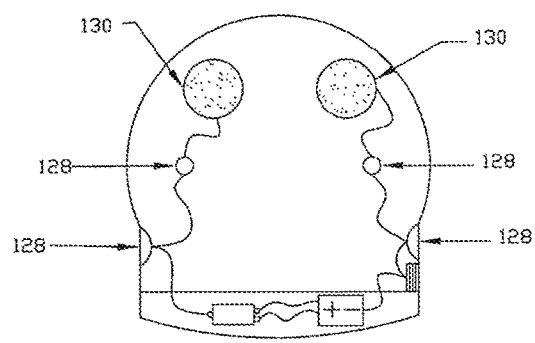
FIG. 18 is a diagram of an athlete's helmet incorporating one or more speakers, according to another embodiment of the present invention.

FIG. 18 illustrates a plurality of speakers 130 can also be incorporated in the helmet for communication with coaches and other staff members.

Figure 19:
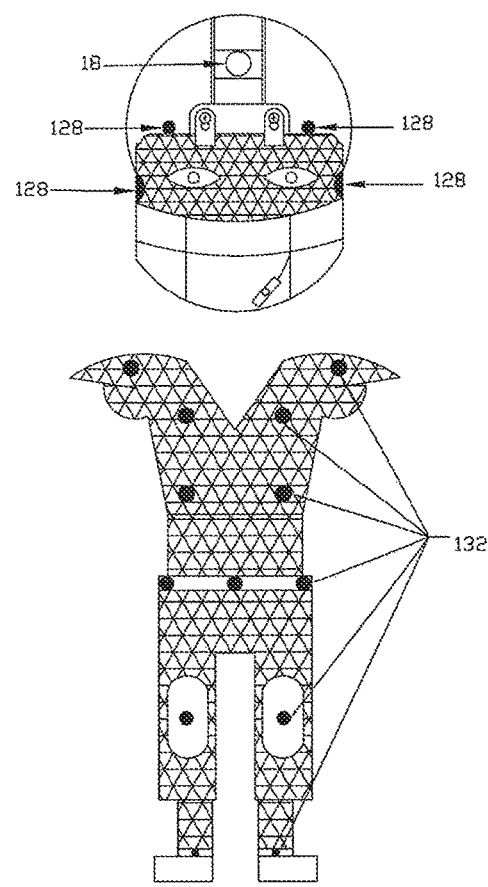
FIG. 19 is a diagram of an athlete's garment incorporating a plurality of pain sensors.

FIG. 19 illustrates a plurality of pain sensors 132 located on an athletic garment 12. If a player is aggressively biting the mouthguard and setting off a pressure sensor, while an eye movement sensor 128 detects eye squinting, the plurality of pain sensors is configured to determine if there is any inflammation in his body. For example, the pain sensors 132 can include pressure and/or lactic acid level sensor used to detect a wearer's muscle state and therefore possible inflammation. The data obtained by the pain sensors 132 can be shown in an alert display showing the body parts of a specific player may possibly be in pain.

Figure 20:
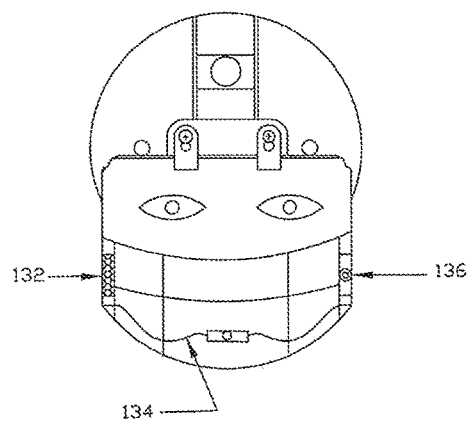
FIG. 20 is a diagram of a helmet including a fluid packet according to another embodiment of the present invention.

FIG. 20 illustrates a helmet including a water packet 132 to store fluid or other liquid. The water packet 132 is configured to dispense fluids to a wearer's mouth through a water line 134. FIG. 20 also has a medication packet 136 to provide aerosol to a mouth guard of a player via a dispense line.

Figure 21:
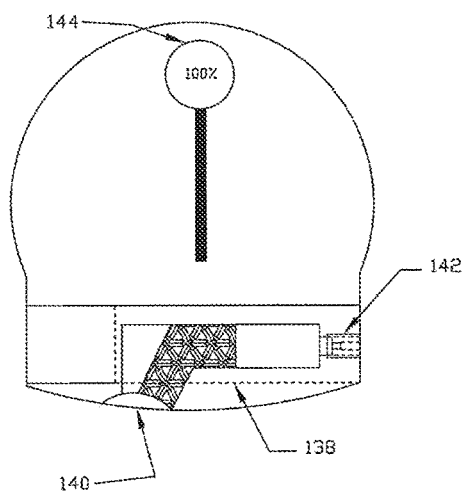
FIG. 21 is a side view of the helmet of FIG. 22.
Figure 22:
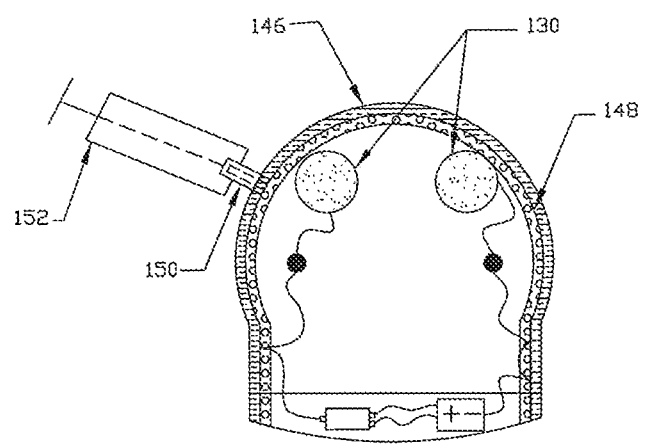
FIG. 22 is a diagram of a helmet, according to another embodiment of the present invention.

FIG. 21 is a side view of the helmet of FIG. 22. A packet door 138 with a door latch is configured to control access to a medication (e.g., inhalation aerosol). A player will push a trigger button 140 to dispatch the aerosol in to a socket 142 configured to dispense the aerosol into the aerosol line and into a mouthguard. A meter 144 shows a total percentage of medication (e.g., inhalation aerosol) available for a player to dispense.

FIG. 22 illustrates another helmet according to another embodiment of the present invention. The helmet includes a foam layer 146 compacted with an air pad 148. The foam layer 146 and the air pad 148 will absorb a physical blow experienced by a player, decreasing the odds or severity of a concussion. The helmet can have a socket 150 located in a top portion on the helmet. The air pad can be filled up via the socket 150 and an air pump 152. An air sensor can also detect air pressure inside the air pads and transmit an alert signal to a coach and/or the wearer. The same design can be used for an athlete garment.

Figure 23:
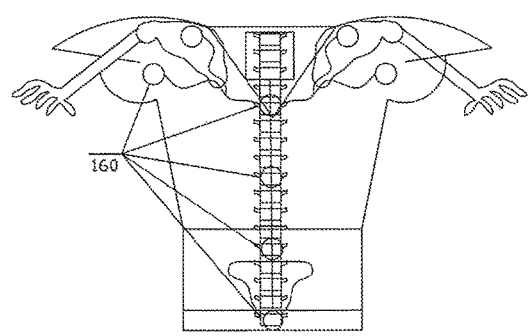
FIG. 23 is a back view of an athlete's garment showing one or more ultrasonic sensors, according to another embodiment of the present invention.

Referring to FIG. 23, an athlete garment 12 having one or more ultrasonic sensors 160 distributed along a wearer's back is shown. The ultrasonic sensors 160 can make an assessment of the alignment of the player's spine, muscles, clavicle, and back before and after a game.

Figure 24:
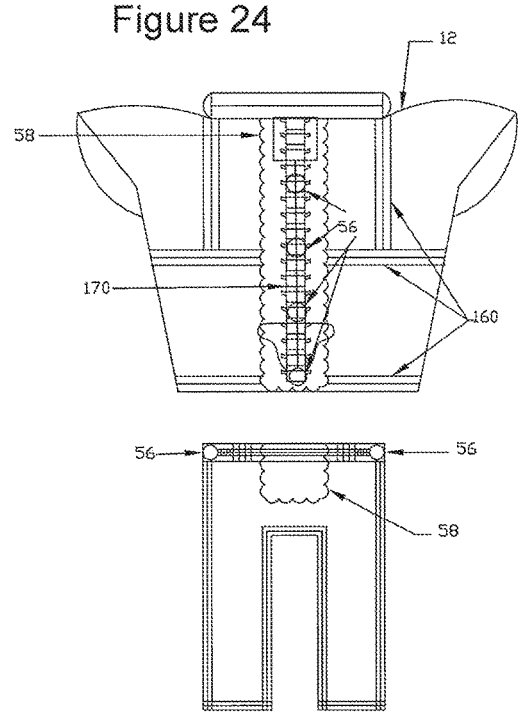
FIG. 24 is a back view of an athlete's garment integrating a spine tension decreasing system, according to another embodiment of the present invention.

FIG. 24 is a back view of an athlete garment 12 having a rubber and foam spine 170 has the shape of a real spine and is made of small rubber and foam ball joints 172 and wrapped by air pad and foam 58. The rubber and foam spine 54 can support weight during athlete movement. The rubber and foam spine 54 also has an air pad and foam 58 to protect a wearer's coccyx and back area.

Figure 25:
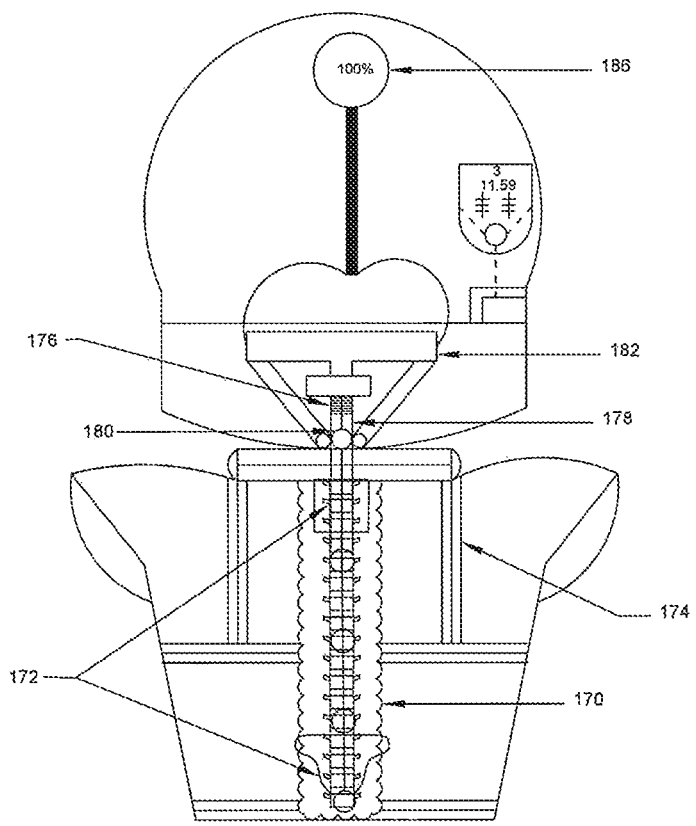
FIG. 25 is a back view of an athlete's garment showing a rubber and foam spine and a plurality of ball joints and axles, according to another embodiment of the present invention.

FIG. 25 is a back view of an athlete garment 12 having a rubber and foam spine 170 integrated with a plurality of ball joints and axles 172. In the depicted embodiment, one or more tensioner straps 174 are used to keep a chest pad and back pad strapped in place. The one or more tensioner straps 174 will also keep back muscles, tendons, and bones intact and decrease vibrations and impacts that may result in injury. A spine tensioner spring 176 is connected to a rear bottom of the helmet by a piston 178 which will decrease the odds the helmet will fly or fall off of the player's head during an impact. The piston 178 will be attached to a rotating neck pivotal ball joint 180 configured to rotate and simulate a player neck movement in a 180 degree manner. The piston 178 and the ball joint 180 will be connected to an oil reserve 182 to allow oil to fluctuate through a rubber spine 170 to penetrate and absorb weight from a helmet, a shoulder pad, a back pad, a chest pad, and the like. The rubber and foam spine with the piston and tensioner spring system decrease injury and make it easier for the player to move when in motion. An oil percentage display unit 186 can show the amount of oil that is left in the oil reserve 182 and send an alert signal when the oil level is running low. Oil can be transferred from an oil reserve 182 through the spring 176 and ball joint 180 to rubber and foam spine 170. A neck tension decrease flap 188 can be considered to expand and contract upon movement with the piston 178, a ball joint 180, a tensioner and spring 176, and rubber and foam spine 170. For example, when a player is in a sitting, supine, or squatting position, the neck tension decrease flap 188 will contract and protect the neck, jugular vein, and collar bone of the player decreasing injury and concussions. If a player should bend his head back, the neck tensioner will contract. The rubber and foam spine 54 can decrease the risk of the athlete sustaining a back injury by transferring weight of garment 12 to the rubber and foam.

Figure 26:
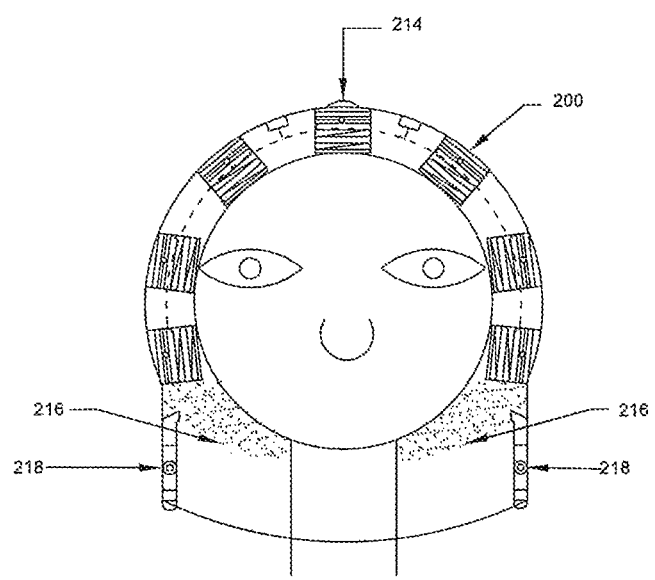
FIG. 26 is a helmet including helix microwave springs with foam, gel, and air pad located around the circumference thereof, according to another embodiment of the present invention.

FIG. 26 illustrates a helmet 200 that includes a plurality of helix microwave springs 210 with foam, gel, and air pad located around the circumference thereof to absorb impacts and dissipate the force. The helmet includes a massage button 214 configured to massage the temple and circumference of a wearer's head. The helmet also includes an air, water, and sunblock mist held in a mist reservoir 216 and can be dispatched upon the face by pressing a release button 218 and the mist will be discharged on the players face and forehead.

Figure 27:
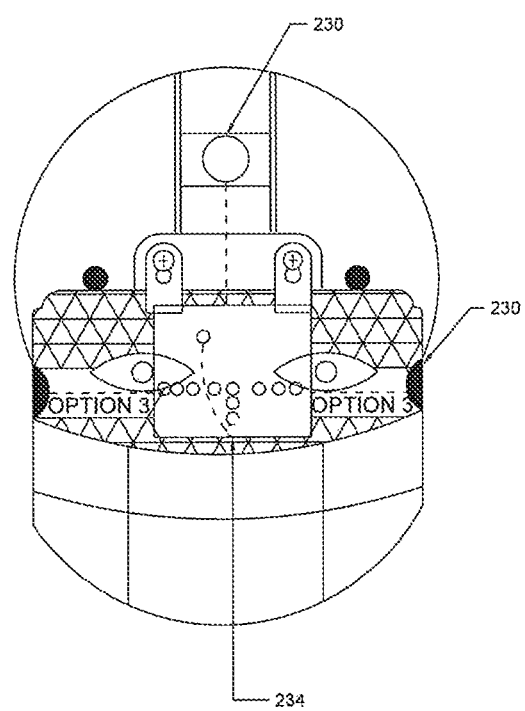
FIG. 27 is a helmet including an astral projection camera and an eye visor, according to another embodiment of the present invention.

FIG. 27 illustrates a helmet that includes an astral projection camera 230 configured to work with an eye visor 232 having a screen 234 applied with a switchable electric film. A viewer can view a game the screen 234 via the eye visor 232 of the helmet. The switchable film can switch between frosted image and clear image. The switchable film enables a viewer to view of video content in privacy as needed. The camera 230 and eye visor 232 covers and protects a wearer's eyes and shows a visual, aural, and verbal astral projection.

The invention can be used by players in basketball, football, soccer, baseball, golf tennis, rugby, skiing, skating, polocrosse and any other suitable sport. The invention can be used in games of the National Basketball Association, National Football Association, Major League Soccer, Major League Baseball, Professional Golf Association, Association of Tennis Professionals, Rugby League Football, Professional Disc Golf Association, Professional Skiing Association, Professional Skaters Association, Professional Skateboard Association, International Skateboard Federation, USA BMX, BMX Canada, American Polocrosse Association, and Men's Bobsled National Team, and the like.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within.

What is claimed is:

1. An athletic wear system comprising:
    an athletic garment;
    a plurality of ultrasonic sensors located on the athletic garment so as to be distributed along a wearer's back;
    a rubber and foam spine on a back of the athletic garment made of rubber and foam ball joints; and
    wherein the plurality of sensors are located along the rubber and foam spine and configured to make an assessment of an alignment of a wearer's spine, muscles, clavicle and back.

2. The system of claim 1, wherein the rubber and foam spine is wrapped by an air pad and foam.

3. The system of claim 1, wherein the air pad and foam includes a section positioned to protect a wearer's coccyx.

4. The system of claim 1, further comprising a helmet; wherein a rear bottom of the helmet is connected to the rubber and foam spine by a spine tensioner spring and a piston.

5. The system of claim 4, wherein the piston is connected to the rubber and foam spine by a neck ball joint.

6. The system of claim 5, further comprising an oil reserve connected to the piston and neck ball joint such that oil from the oil reserve can flow through the rubber and foam spine.

7. The system of claim 6, further comprising a display connected to the helmet configured to indicate an amount of oil left in the oil reserve.

8. The system of claim 7, wherein the display includes an alarm configured to send an alert signal when the amount of oil is running low.

* * * * *